(12) United States Patent
Koopman et al.

(10) Patent No.: US 11,813,631 B2
(45) Date of Patent: Nov. 14, 2023

(54) COLLAR AND ASSEMBLIES INCLUDING SAME, FOR APPLICATORS, SYRINGES AND THE LIKE

(71) Applicant: Prodigy Instruments Pty Ltd, Bondi Junction (AU)

(72) Inventors: Harry Shane Koopman, Sydney (AU); Matthew Phillips, Sydney (AU)

(73) Assignee: PRODIGY INSTRUMENTS PTY LTD., Bondi Junction (AU)

( * ) Notice: Subject to any disclaimer, the term of this patent is extended or adjusted under 35 U.S.C. 154(b) by 371 days.

(21) Appl. No.: 16/870,377

(22) Filed: May 8, 2020

(65) Prior Publication Data

US 2020/0360954 A1    Nov. 19, 2020

(30) Foreign Application Priority Data

May 14, 2019    (AU) .................................. 2019901643

(51) Int. Cl.
  *B05B 15/18*    (2018.01)
  *B65D 83/00*    (2006.01)
  *A61M 39/10*    (2006.01)
  *A61M 5/31*    (2006.01)
(52) U.S. Cl.
  CPC ........... *B05B 15/18* (2018.02); *A61M 5/3134* (2013.01); *A61M 39/10* (2013.01); *B65D 83/0005* (2013.01); *A61M 2039/1077* (2013.01)

(58) Field of Classification Search
  CPC .................... A61M 5/345; A61M 5/31; A61M 2005/3104; A61M 39/20; A61M 39/10; A61M 2039/1077; A61M 5/3134; A61M 5/31526; A61M 5/31581; B05B 15/18; B65D 83/0005
  See application file for complete search history.

(56) References Cited

U.S. PATENT DOCUMENTS

2015/0034194 A1* 2/2015 Uber, III ............... A61M 39/18
                                                              137/797
2015/0105737 A1* 4/2015 Lopez ................... A61M 39/10
                                                              604/249

FOREIGN PATENT DOCUMENTS

KR    20140141279 A  * 12/2014  .......... A61M 5/3202
KR    20130062863 A  *  2/2015  ............. A61M 5/32

* cited by examiner

*Primary Examiner* — Brandy S Lee
(74) *Attorney, Agent, or Firm* — McAndrews Held & Malloy, Ltd.

(57) ABSTRACT

A collar for reinforcing a barrel outlet spout of an applicator, syringe or the like, the barrel having a substantially cylindrical main body, with the outlet spout at one end thereof, wherein the collar includes: a spout engagement portion; and a main body engagement portion.

19 Claims, 4 Drawing Sheets

COLLAR AND ASSEMBLIES INCLUDING SAME, FOR APPLICATORS, SYRINGES AND THE LIKE

CROSS-REFERENCE TO RELATED APPLICATION

This application claims benefit of priority from Australian Patent Application No. AU2019/901643, filed on, May 14, 2019, titled "Collar and assemblies including same, for applicators, syringes and the like," which is incorporated herein by reference in its entirety.

FIELD OF THE INVENTION

The present invention relates to collars, and, in particular, to retaining collars for assemblies (like head or adapter assemblies) that are typically secured to the barrel of an applicator, syringe or the like.

BACKGROUND OF THE INVENTION

Typical applicators and syringes include a barrel with an outlet spout, and a plunger/piston configured to drive the contents of the barrel out of the spout. Often, depending on the particular application, a needle, nozzle or other outlet fitting may be required at the outlet spout. To facilitate securement of a needle, nozzle etc., to the outlet spout, an adapter is generally used. The adapter allows a secure fluid connection between the barrel outlet spout and any corresponding fitting (e.g. needle/nozzle).

One particular type of adapter is a luer lock adapter, which allows a fluid connection with a luer configured needle hub. In some examples, luer lock adapters may comprise a two part assembly. In a typical two-part assembly, a male inner luer lock stem member is first located within the outlet spout, and subsequently, a retaining nut or collar then secured over the male inner luer lock stem. The retaining nut or collar engages with the outer thread of the outlet spout and retains the male inner luer lock stem member within the spout. The retaining nut or collar also includes an inner luer thread, such that, in combination with the male inner luer lock stem member, a luer lock connector is provided, that can securely engage with a luer configured needle hub. FIG. 1 shows one example of a two-part luer lock assembly mounted to the barrel of an applicator. The retaining collar or nut is enlarged at FIGS. 3 and 4.

However, prior art luer lock adapters, like that shown in FIG. 1, are prone to failure. In particular as applicator/syringe barrels are typically formed of a polymer material, like polypropylene, the joint connecting the barrel spout to the main body of the barrel is often weak and prone to breakage. This is exacerbated when a collar, like that shown in FIGS. 3 and 4, is secured to the spout. Any impact on the collar, which is typically relatively heavy and formed of a metallic material, places stress on the joint at the outlet spout, and often, the spout snaps off the barrel. This is obviously disadvantageous and dangerous, as the barrel of the applicator is no longer fit for purpose, and the contents thereof, which may be toxic, are unintentionally released.

The present invention seeks to provide improved collars for reinforcement that may implemented as part of adapter assemblies or otherwise.

Any reference herein to known prior art does not, unless the contrary indication appears, constitute an admission that such prior art is commonly known by those skilled in the art to which the invention relates, at the priority date of this application.

BRIEF DESCRIPTION OF THE DRAWINGS

A detailed description of a preferred embodiment will follow, by way of example only, with reference to the accompanying drawings, in which.

SUMMARY OF THE INVENTION

Figure 1:
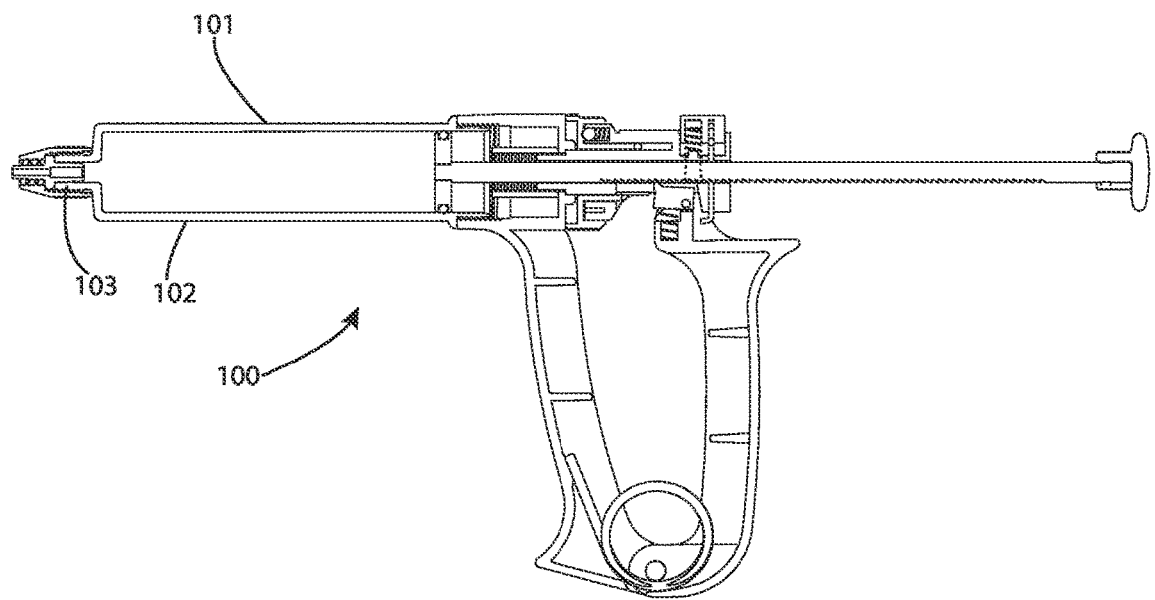
FIG. 1 a cross sectional side view of one example of a barrel and plunger type applicator to which the collar according to one example of the invention may be attached.
Figure 2:
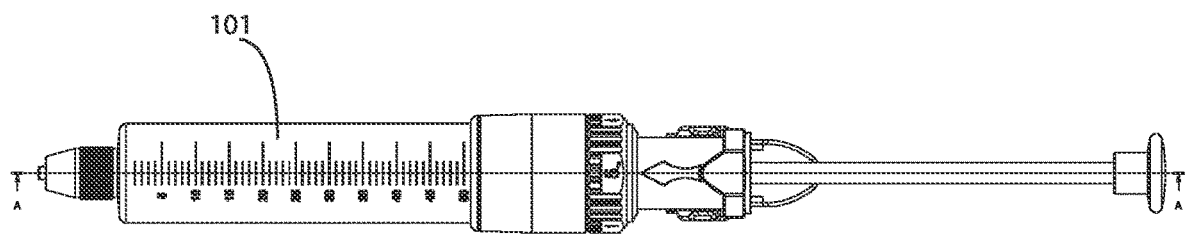
FIG. 2 is a top view of the applicator shown in FIG. 1.
Figure 3:
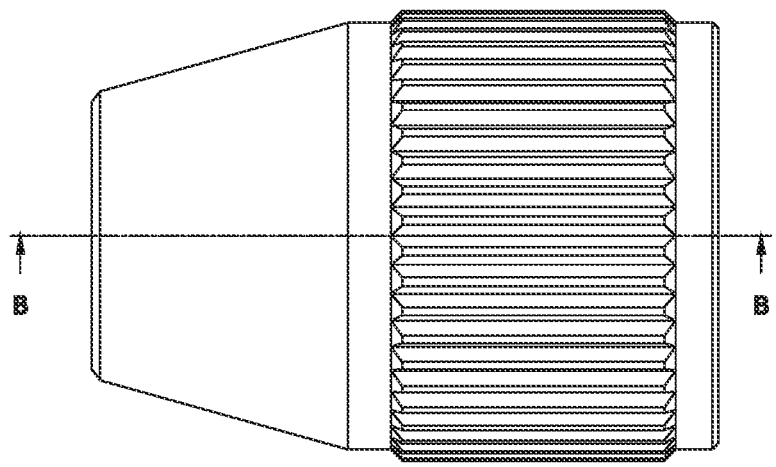
FIG. 3 is a side view of one example of a prior art collar.
Figure 4:
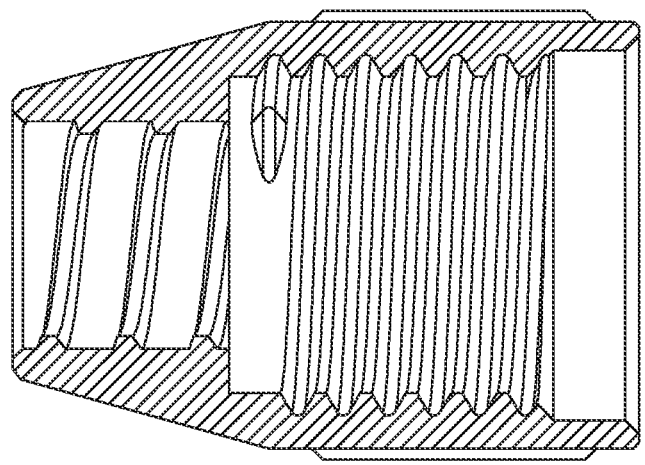
FIG. 4 is as a cross-sectional side view along the line B-B of the prior art collar as shown in FIG. 3.
Figure 5:
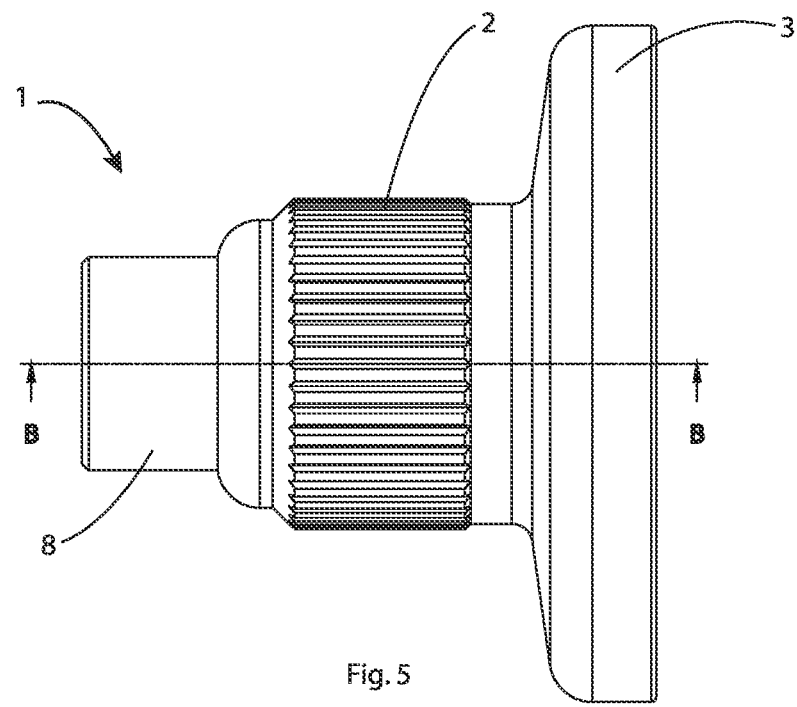
FIG. 5 is a side view of a collar according to one example of the invention.
Figure 6:
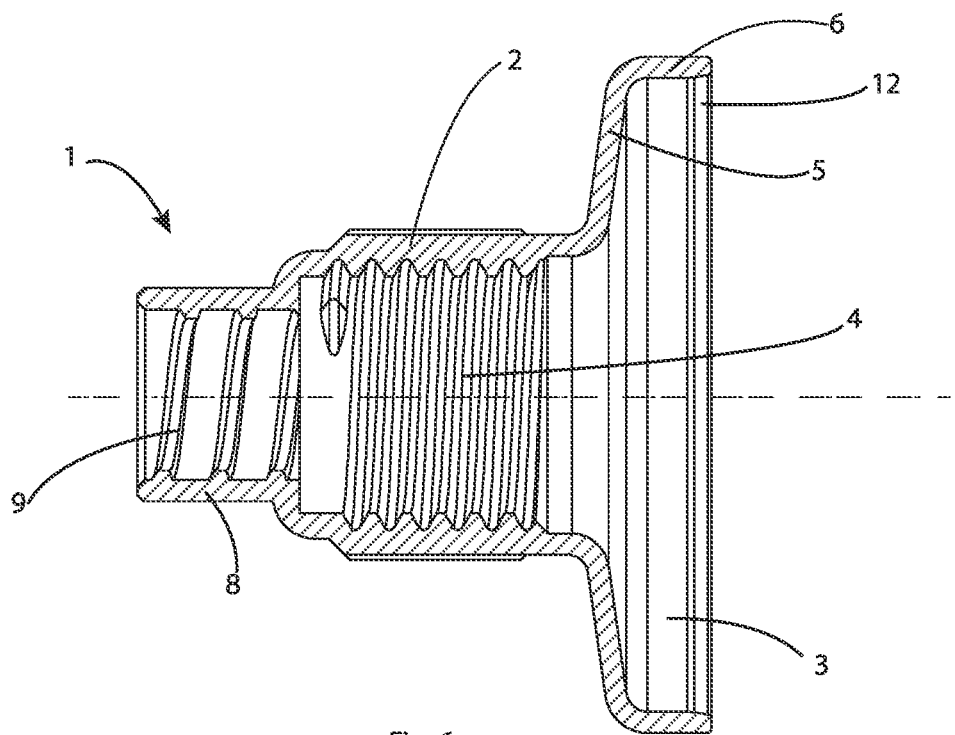
FIG. 6 is a cross sectional side view along the line B-B of the collar as shown in FIG. 5.
Figure 7:
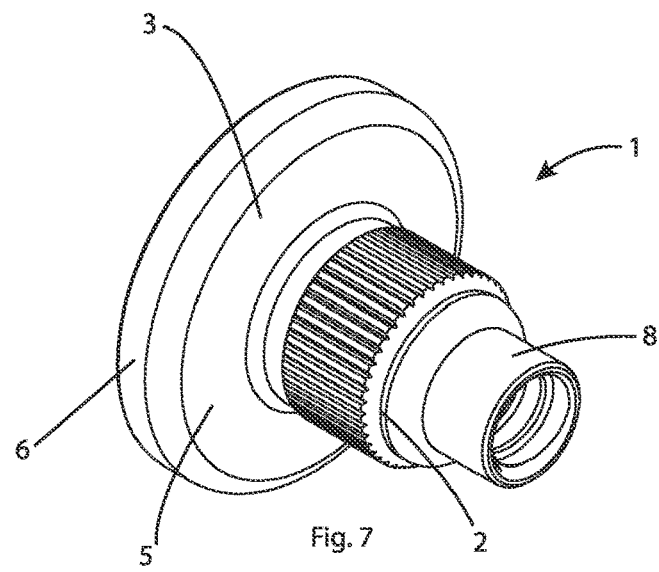
FIG. 7 is a perspective view of the collar of FIG. 5.
Figure 8:
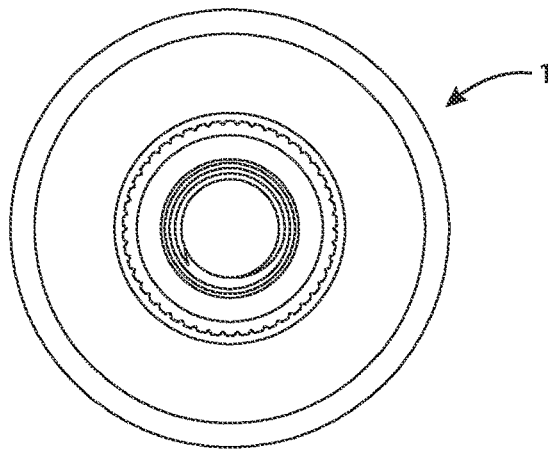
FIG. 8 top view of the collar of FIG. 5.

In a one broad form the present invention provides, a collar for reinforcing a barrel outlet spout of an applicator, syringe or the like, the barrel having a substantially cylindrical main body, with the outlet spout at one end thereof, wherein the collar includes: a spout engagement portion; and a main body engagement portion.

In one form, the spout engagement portion includes an internally threaded passage therethrough configured to receive a threaded outlet spout.

In one form, the main body engagement portion extends from a spout receiving end of the spout engagement portion. In one form, the main body engagement portion is configured to engage the curved outer wall of the main body of the barrel. In one form, the main body engagement portion includes a rim adapted to encircle the barrel. In one form, the main body engagement portion provides a substantially cylindrical recess adapted to fit the spout containing end of the barrel main body therein.

In one form, a flange extends inwardly from the non-spout receiving end of the spout engagement portion, the flange for clamping an outlet fitting in fluid connection with the outlet spout.

In one form, the collar further includes an adapter portion, the adapter portion opposite the spout receiving side of the collar, the adapter portion for engaging a corresponding adapter fitting. In one form, the adapter portion includes a substantially cylindrical passage with an internal luer thread. In one form, the adapter portion has a smaller internal diameter than the spout engagement portion.

In one form, the collar includes an integral outlet nozzle. In one form, the collar includes an integral needle. In one form, the collar includes an integral luer lock connector, adapted to receive a luer configured needle hub.

In a further broad form, the present invention provides an adapter assembly for securement to the barrel of an applicator, syringe or the like, the barrel having a substantially cylindrical main body, with an outlet spout at one end, wherein the adapter assembly includes: an outlet fitting configured to be located in fluid connection with the outlet spout; and a collar as described in any one of the above forms, the collar configured to collar the outlet fitting and engage the barrel, so as to retain the outlet fitting in fluid connection with the outlet spout. In one form, the outlet fitting is a male luer lock stem member.

In a further broad form, the present invention provides a luer lock adapter assembly for securement to the barrel of an applicator, syringe or the like, the barrel having a substantially cylindrical main body, with an outlet spout at one end, wherein the adapter assembly includes: a male inner luer lock stem member configured to be located within the outlet spout; and a collar as described in any one of the above forms with an adapter portion that defines a substantially cylindrical passage with an internal luer thread, the collar configured to collar the male inner luer lock member and engage the barrel, so as to retain the male inner luer lock stem member within the outlet spout such that it aligns with the luer thread of the adapter portion of the collar, the combination of same providing a luer lock connector.

In a further broad form, the present invention provides a head assembly for securement to the barrel of an applicator, syringe or the like, the barrel having a substantially cylindrical main body, with an outlet spout at one end, wherein the head assembly includes: a terminal outlet member; and a collar as described in any one of the above forms, configured to collar the terminal outlet member and engage the barrel so as to retain the terminal outlet member in fluid connection with outlet spout. In one form, the terminal outlet member is a nozzle. In one form, the terminal outlet member is a hub mounted needle.

In a further broad form, the present invention provides a plunger and barrel type applicator including collar as described in any one of the above forms.

In a further broad form, the present invention provides a syringe including a collar as described in any one of the above forms.

DETAILED DESCRIPTION

Embodiments of the invention provide a collar or nut for reinforcing a barrel outlet spout of an applicator, syringe or the like. As would be appreciated to a skilled person, barrels for applicators (e.g. plunger and barrel type) and syringes have a substantially cylindrical main body, with an outlet spout at one end. The collars/nuts as described herein include a spout engagement portion and a main body engagement portion.

Generally, as the outlet spout of an applicator/syringe barrel is typically threaded, the spout engagement portion of the collar typically includes and internally threaded passage to allow engagement with the outlet spout.

The main body engagement portion extends from the spout receiving end of the spout engagement portion and is generally configured to engage the curved outer wall of the barrel main body. Typically, the main body portion includes a rim adapted to encircle the barrel. In some forms, the main body engagement portion provides a substantially cylindrical recess adapted to fit the spout containing end of the barrel main body therein.

It will be appreciated that main body engagement portion typically extends form the spout engagement portion over the shoulders of the main body of the barrel to engage the curved side wall thereof. This provide provides advantages in that the joint between the outlet spout and main body of the barrel is protected. Stress due to impact on the collar, is rather directed to the more resilient main body.

At the non-spout receiving end, an inwardly extending flange may be provided that allows for clamping of an outlet fitting in fluid connection with the outlet spout. For example the outlet fitting may be part of a multi-part adapter assembly. Alternatively, a terminal outlet member may be clamped, such as, for example, a nozzle or a hub mounted needle.

Alternatively or additionally, the collar also includes an adapter portion at the distal or non-spout receiving side of the spout engagement portion. The adapter portion typically configured for engagement of a corresponding adapter fitting. For example the adapter portion may form part or all of a luer lock connector that is configured to receive a luer lock configured needle hub. In one particular example, of the adapter portion may include an internal luer thread and the collar may clamp a male luer lock stem member such that the combination of same provides a luer lock connector.

Typically, the main body engagement portion, spout engagement portion and adapter portion define substantially cylindrical passages that are axially aligned. It will be appreciated that the main body engagement portion typically has the largest internal diameter as it is configured to fit the shoulders of the applicator/syringe barrel. The spout receiving portion typically has a smaller diameter to securely engage the outlet spout. The adapter portion is typically smaller again, such that the flange connecting the spout engagement portion and adapter portion may be used to clamp an outlet fitting (or other part) to the outlet spout.

In some forms the collar may not include an adapter portion and/or may not be configured to clamp an outlet fitting (or other part). Instead, the collar may include an integral terminal outlet member such as, for example, and integral outlet nozzle or an integral needle.

The collar may also be implemented as part of a multi-part adapter assembly for securement of a corresponding adapter fitting to the barrel. The collar may for example be configured to clamp other parts of the assembly (e.g. outlet fittings) in fluid connection with the outlet spout. The combination of the collar and other clamped parts cooperating to provide the adapter assembly.

For example, the collar may form part of a luer lock adapter assembly. In such forms, the collar may be configured to clamp a male inner luer lock stem member within the outlet spout. The adapter portion of the collar including an inner luer thread such that once secured to the barrel, the thread aligns with the retained male inner luer lock stem member so that the combination thereof provides a luer lock connector capable of engaging a corresponding luer configured needle hub.

The collar may alternatively form part of a head assembly. The collar acting to clamp a terminal outlet member in fluid connection with the outlet spout. For example, the terminal outlet member may a nozzle or a hub mounted needle. It will be appreciated that the invention may also embodied as a 'plunger and barrel' type applicator, or syringe that includes a collar as described herein either integrally or as a releasably attached part.

One particular form of a collar according to an example of the invention is shown in FIGS. 5 to 9. The collar (1) is part of a luer lock adapter assembly that also provides reinforcement to an applicator barrel outlet spout. The applicator may be a plunger and barrel type applicator, such as, for example, that shown in FIG. 1. As shown in FIG. 1, the applicator (100) includes a barrel (101) having a substantially cylindrical main body (102) with an outlet spout (103) at one end.

The collar (1) includes a spout engagement portion (2) and a barrel main body engagement portion (3). The spout engagement portion (2) has a threaded cylindrical passage (4) therethrough configured to receive the threaded outlet spout (e.g. 103) of a barrel (e.g. 101) of an applicator (e.g. 100). The main body engagement portion (3) is provided by an annular flange (5) that extends outwardly from the spout receiving end of the spout engagement portion (2) and a rim (6) that projects from the outer periphery of the flange (5). The main body engagement portion (3) is thus substantially cup-shaped and defines a substantially cylindrical recess.

Figure 9:
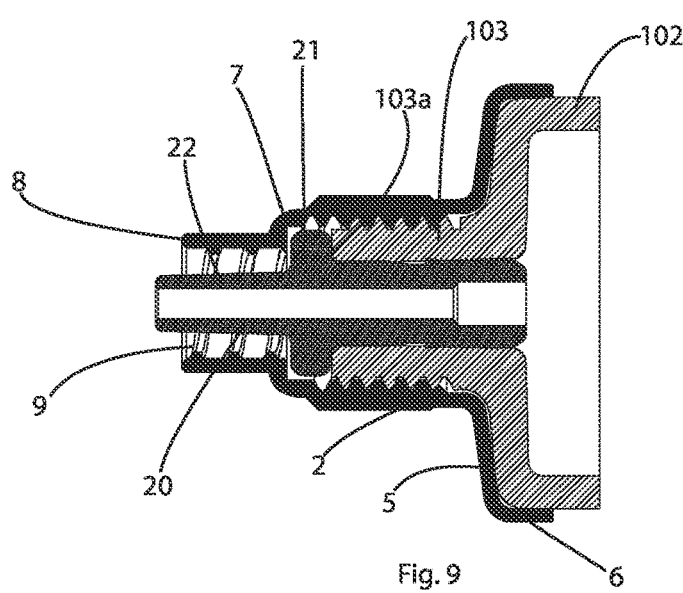
FIG. 9 is a cross sectional side view of the collar according to one example when secured to the barrel of an applicator.

As shown in FIG. 9, the main body engagement portion (3) is configured to receive the width of the spout containing end of the barrel (e.g. 101) therein as the outlet spout (e.g. 103) is tightened to the within the spout engagement portion (2). In particular, the main body engagement portion is configured to extend over the shoulders of a barrel (e.g. 101), such that the rim (6) contactingly engages the outer curved surface of the barrel once the collar (1) is secured. The lip (12) of the rim (6) is bevelled on its internal side so as to facilitate insertion of the main body (e.g. 102) of the barrel. Having a collar (1) that extends from the outlet spout (e.g. 103) to the main body (e.g. 102), and in particular beyond the shoulders of the main body to contact the curved side wall thereof, provides that the joint between the outlet spout and the barrel is protected. When the collar is impacted or bumped accidently, force/stress is rather directed to the more resilient main body of the barrel.

To provide the luer lock adapter/connector, the collar (1) is used in combination with an inner male luer lock stem member (20). In typical use, the inner male luer lock stem member is first placed within the outlet spout (e.g. 103) of a barrel (e.g. 101). An outer flange (21) of the stem member (20) abuts the rim (e.g. 103a) of the outlet spout (e.g. 103) prohibiting entry of the male luer lock stem member (20) into the barrel (e.g. 101). The collar (1) is then placed over the male luer lock stem member clamping the male luer lock member (20) against the rim (103a) of the spout (103).

A flange (7) extends inwardly from the non-spout receiving end of the spout engagement portion (2) to abut against the flange (21) of the male luer lock stem member (20) as the collar (1) is tightened to the barrel. From the flange (7), extends an adapter portion (8) which defines a cylindrical passage that is internally threaded with a luer thread (9). In typical use, the stem (22) of the male luer lock stem member (20) extends into the adapter portion (8) such that the combination of the stem (20) with the luer thread (9) provides a luer lock connector that is able to receive a corresponding luer configured needle hub (not shown).

To facilitate tightening of the collar (1) the spout receiving portion (2) includes grooves (11) on the outside surface thereof. The collar (1) is typically form of a metallic material but it will be appreciated that it may be formed of a wide variety of materials such as, for example, composite or polymer materials.

It will also be appreciated that whilst presently described embodiment relates to a collar used as part of a luer lock adapter assembly, the reinforcement collar may be configured for use with a range of outlet fittings and/or as part of other adapter assemblies and/or may incorporate integral outlet fittings. For example the adapter portion may be configured allow snap-locking with a needle hub or nozzle, or alternatively the collar may include an integral needle or nozzle.

Where ever it is used, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The invention claimed is:

1. A collar for reinforcing a barrel outlet spout of a barrel of an applicator or a syringe, the barrel comprising a substantially cylindrical main body having an outer surface, the barrel outlet spout being at one end of the main body and having an outer surface with a threaded section thereon, wherein the collar comprises:
   a spout engagement portion having opposed ends with an internal passage extending therethrough between the ends, the internal passage having an inner surface with a threaded section thereon;
   a main body engagement portion that extends from one of the ends of the spout engagement portion, the main body engagement portion configured to engage with the outer surface of the main body of the barrel when the collar is in a fitted position on the barrel; and
   adapter portion, the adapter portion at the other of said ends of the spout engagement portion for engaging a corresponding adapter fitting, the adapter portion, the spout engagement portion, and the main body engagement portion being a one piece structure,
wherein the threaded section on the spout engagement portion is configured so as to cooperate with the threaded section on the outer surface of the barrel outlet spout so as to secure the collar to the barrel in the fitted position.

2. The collar as claimed in claim 1, wherein the main body engagement portion of the collar includes a rim adapted to encircle the outer surface of the main body of the barrel when the collar is in the fitted position.

3. The collar as claimed in claim 1, wherein the main body engagement portion provides a substantially cylindrical recess adapted to fit said one end of the barrel main body therein when the collar is in the fitted position.

4. The collar as claimed in claim 1, wherein a flange extends inwardly from the other of the ends of the spout engagement portion, the flange arranged for clamping an outlet fitting to the outlet spout.

5. The collar as claimed in claim 1, wherein the adapter portion includes a substantially cylindrical passage with an internal luer thread.

6. A luer lock adapter assembly for securement to the barrel of an applicator or a syringe, the barrel having a substantially cylindrical main body, with an outlet spout at one end, wherein the adapter assembly includes:
   a male inner luer lock stem member configured to be located within the outlet spout; and
   the collar as claimed in claim 5, the collar configured to retain the male inner luer lock stem member within the outlet spout such that it aligns with the luer thread of the adapter portion of the collar, the combination of same providing a luer lock connector.

7. A plunger and barrel type applicator including the luer lock adapter assembly as claimed in claim 6.

8. A syringe including the luer lock adapter assembly as claimed in claim 6.

9. The collar as claimed in claim 1, wherein the adapter portion has a smaller internal diameter than the internal passage of the spout engagement portion, so as to provide for an inwardly extending flange.

10. The collar as claimed in claim 1, wherein the collar includes an integral outlet nozzle.

11. The collar as claimed in claim 1, wherein the collar includes an integral needle.

12. The collar as claimed in claim 1, wherein the collar includes an integral luer lock connector, adapted to receive a luer configured needle hub.

13. An adapter assembly for securement to the barrel of an applicator or a syringe, the barrel having a substantially cylindrical main body, with an outlet spout at one end, wherein the adapter assembly includes:
   an outlet fitting configured to be located at the outlet spout; and
   the collar as claimed in claim 1, the collar configured to retain the outlet fitting at the outlet spout.

14. The adapter assembly as claimed in claim 13, wherein the outlet fitting is a male luer lock stem member.

15. A head assembly for securement to the barrel of an applicator, or a syringe, the barrel having a substantially cylindrical main body, with an outlet spout at one end, wherein the head assembly includes:
   a terminal outlet member configured to be located at the outlet spout; and
   the collar as claimed in claim 1, the collar configured to retain the terminal outlet member at the outlet spout.

16. The head assembly as claimed in claim 15, wherein the terminal outlet member is a nozzle.

17. The head assembly as claimed in claim 15, wherein the terminal outlet member is a hub mounted needle.

18. A plunger and barrel type applicator including the collar as claimed in claim 1.

19. A syringe including the collar as claimed in claim 1.

* * * * *